United States Patent
Hayashi et al.

[11] 4,018,812
[45] Apr. 19, 1977

[54] 16-METHYLENE-PROSTAGLANDIN COMPOUNDS

[75] Inventors: Masaki Hayashi; Seiji Kori, both of Takatsuki; Hajimu Miyake, Suita, all of Japan

[73] Assignee: Ono Pharmaceutical Co., Ltd., Osaka, Japan

[22] Filed: May 13, 1976

[21] Appl. No.: 685,953

[30] Foreign Application Priority Data
June 16, 1975 United Kingdom ............ 25591/75

[52] U.S. Cl. .................... 260/468 D; 260/345.7; 260/345.8; 260/347.3; 260/347.4; 260/448.8 R; 260/488 R; 260/514 D; 536/1; 424/305; 424/317

[51] Int. Cl.² ........................................ C07C 177/00

[58] Field of Search .................. 260/468 D, 514 D

[56] References Cited
UNITED STATES PATENTS
3,953,495  4/1976  Hayashi et al. ................ 260/468 D Primary Examiner—Robert Gerstl
Attorney, Agent, or Firm—Albert H. Graddis; Frank S. Chow

[57] ABSTRACT

A compound of the formula:

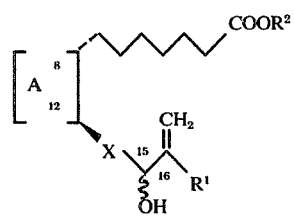

wherein A represents a grouping of the formula:

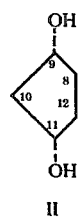

or

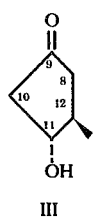

II            III

, $R^1$ represents a hydrogen atom or a straight- or branched-chain alkyl group containing from 1 to 6 carbon atoms, $R^2$ represents a hydrogen atom or a straight- or branched-chain alkyl group containing from 1 to 12 carbon atoms, X represents trans-vinylene or ethylene, and the wavy line indicates attachment of the hydroxy radical in α- or β-configuration and cyclodextrin clathrates thereof and, when $R^2$ represents a hydrogen atom, non-toxic salts thereof. These compounds exhibit characteristic prostaglandin activity.

5 Claims, No Drawings

16-METHYLENE-PROSTAGLANDIN COMPOUNDS

THIS INVENTION relates to 16-methylene-prostaglandin compounds to processes for their preparation and pharmaceutical compositions containing them.

In the specification of our U.S. Pat. Ser. No. 3,953,495 (granted on application Ser. No. 501,548 filed Aug. 29, 1974) we have described inter alia new prostaglandin analogues of the general formula:

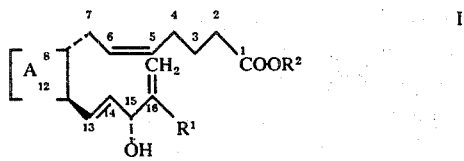

(wherein A represents a grouping of the formula:

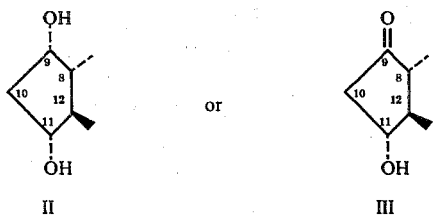

, $R^1$ represents a hydrogen atom or a straight- or branched-chain alkyl group containing from 1 to 6 carbon atoms, $R^2$ represents a hydrogen atom or a straight- or branched-chain alkyl group containing from 1 to 12 carbon atoms, and the double bonds between $C_5-C_6$ and $C_{13}-C_{14}$ are cis and trans respectively), which possess useful pharmacological properties. The dotted lines in the foregoing formulae denote, in accordance with generally accepted rules of nomenclature, that the attached hydroxy radicals lie behind the general plane of the ring system, i.e. that the hydroxy radicals are in α-configuration.

As a result of further research and experimentation it has now been found that when the $C_5-C_6$ double bond, and optionally also the $C_{13}-C_{14}$ double bond, of compounds of general formula I is, or are, replaced by ethylene (i.e. —$CH_2CH_2$—), and the hydroxy radical attached to $C_{15}$ is in α-configuration or in β-configuration, i.e. the hydroxy radical lies in front of the general plane of the ring system, the resulting $PGF_{1\alpha}$ and $PGE_1$, and 13,14-dihydro-$PGF_{1\alpha}$ and -$PGE_1$, compounds also possess useful pharmacological properties.

The present invention is accordingly concerned with new prostaglandin analogues of the general formula:

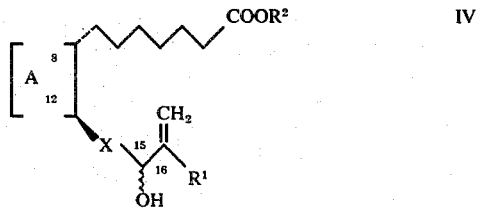

(wherein A, $R^1$ and $R^2$ are as hereinbefore defined, X represents trans-vinylene (i.e. —CH=CH—) or ethylene, and the wavy line ⌇ indicates attachment of the hydroxy radical in α- or β-configuration) and cyclodextrin clathrates thereof and, when $R^2$ represents a hydrogen atom non-toxic (e.g. sodium) salts thereof. Preferably A represents a grouping of formula III, $R^1$ represents the n-butyl group, $R^2$ represents a hydrogen atom or the methyl group, and the hydroxy radical attached to $C_{15}$ is in α-configuration.

The present invention is concerned with all compounds of general formula IV in the 'natural' form or its enantiomeric form, or mixtures thereof, more particularly the racemic form consisting of equimolecular mixtures of natural and its enantiomeric form.

As will be apparent to those skilled in the art, the compounds depicted in general formula IV have at least four centres of chirality, these four centres of chirality being at the cyclopentane ring carbon atoms of group A identified as 8 and 12, at the position identified as 11 of the cyclopentane rings in formulae II and III, and at the $C_{15}$ carbon atom which has attached to it a hydroxy group. A further centre of chirality occurs when the group A carries a hydroxy group on the carbon atom in position 9 (i.e. when the ring is that of formula II), and further centres of chirality may occur in alkyl groups represented by the symbol $R^1$. The presence of chirality leads, as is well known, to the existence of isomerism. However, the compounds of general formula IV all have such a configuration that the side-chains attached to the ring carbon atoms in the positions identified as 8 and 12 are trans with respect to each other. Accordingly, all isomers of general formula IV, and mixtures thereof, which have those side-chains attached to the ring carbon atoms in positions 8 and 12 in the trans-configuration are to be considered within the scope of general formula IV.

The prostaglandin analogues of general formula IV, and cyclodextrin clathrates and non-toxic salts thereof, possess the valuable pharmacological properties typical of prostaglandins in a selective fashion including, in particular, hypotensive activity, inhibitory activity on gastric acid secretion and gastric ulceration, inhibitory activity on blood platelet aggregation, coronary vasodilator activity and bronchodilator activity and are useful in the treatment of hypertension, in the treatment of gastric ulceration, in the treatment of disorders of the peripheral circulation, in the prevention and treatment of cerebral thrombosis, myocardial infarction, angina pectoris and ischemic heart disease, and in the treatment of asthma. For example, in standard laboratory screening tests, (i) when administered intravenously to the allobarbital-anaesthetized dog, 16-methylene-$PGE_1$ methyl ester and 16-methylene-13,14-dihydro-15(ξ)-$PGE_1$ produce, respectively, falls in blood pressure of 10 mm.Hg, 24 mm.Hg and 44 mm.Hg and 18 mm.Hg, 24 mm.Hg and 36 mm.Hg, respectively, lasting 8 minutes, 16 minutes and 27 minutes and 7 minutes, 8 minutes and 16 minutes, respectively, at doses of 0.02, 0.05 and 0.1 and 0.05, 0.1 and 0.2 μg./kg. animal body weight respectively; (ii) when administered orally to the conscious spontaneously hypertensive rat, 16-methylene-$PGE_1$ methyl ester produces falls in blood pressure of 61 mm.Hg, 58 mm.Hg, 56 mm.Hg and 45 mm.Hg, respectively, at 0.5, 1, 3 and 5 hours after administration, respectively, at a dose of 500 μg./kg. animal body weight, falls in blood pressure of 43 mm.Hg, 34 mm.Hg, 26 mm.Hg and 17 mm.Hg, respectively, at 0.5, 1, 3 and 5 hours after administration, respectively, at a dose of 200 μg./kg. animal body weight, falls in blood pressure of 52 mm.Hg, 30 mm.Hg, 32 L mm.Hg, 22 mm.Hg and 13 mm.Hg, respectively at 0.5, 1, 3, 5 and 7 hours after administration, respectively, at a dose of 100 μg./kg. animal body weight and falls in blood pressure of 36 mm.Hg, 16 mm.Hg and 13 mm.Hg, respectively, at 0.5, 1 and 3 hours after administration, respectively, at a dose of 50 μg./kg. animal body weight and 16-methylene-13,14-dihydro-15(ξ)-PGE$_1$ produces falls in blood pressure of 23 mm.Hg, 13 mm.Hg and 17 mm.Hg, respectively, at 0.5, 1 and 3 hours after administration, respectively, at a dose of 200 μg./kg. animal body weight; (iii) in gastric stress ulceration in rats produced according to the method of Takagi and Okabe [Jap. J. Pharmac. 18, 9-18 (1968)], 16-methylene-PGE$_1$ methyl ester and 16-methylene-13,14-dihydro-15(ξ)-PGE$_1$ produce, respectively, a 69.82% and 79.2% inhibition of stress ulceration and a 12.41% and 59.54% inhibition of stress ulceration, respectively, when administered orally at doses of 100 and 200 μg./kg. animal body weight and 100 and 200 μg./kg. animal body weight, respectively, to rats soaked in a water bath at 19° C. for 6 hours; (iv) 16-methylene-PGE$_1$ methyl ester and 16-methylene-13,14-dihydro-15(ξ)-PGE$_1$ produce an increase in gastric acid pH from 2.0-2.5 to at least 4.0 in 50% of pentagastrin-treated rats when perfused into the stomach at rates of 0.25-0.5 and ≤ 5μg./animal/minute, respectively, (v) 16-methylene-PGE$_1$ methyl ester produces 50% inhibition of adenosine diphosphate-induced blood platelet aggregation in platelet-rich plasma of humans at a dose of $1.50 \times 10^{-2}$ μg./ml. in comparison with controls and 16-methylene-PGE$_1$ methyl ester and 16-methylene-13,14-dihydro-15(ξ)-PGE$_1$ produce 50% inhibition of adenosine diphosphate-induced blood platelet aggregation in platelet-rich plasma of rats at doses of $9.2 \times 10^{-3}$ and $1.72 \times 10^{-1}$ μg./ml., respectively, in comparison with controls; (vi) in the rabbit isolated heart, according to the method of Langendorff, D., Pflugers Arch. Ges. Physiol., 61, 291, 1895., 16-methylene-PGE$_1$ methyl ester produces 23.7%, 88.2% and 158.1% increases in coronary flow, respectively, at doses of 0.03, 0.1 and 0.3 μg., respectively, and 16-methylene-13,14-dihydro-15(ξ)-PGE$_1$ produces 22.2% and 61.1% increases in coronary flow, respectively, at doses of 0.1 and 0.3μg. respectively; and (vii) on isolated guinea pig tracheal muscle using the method of Magnus and a cumulative dose technique, 16-methylene-PGE$_1$ methyl ester and 16-methylene-13,14-dihydro-15(ξ)-PGE$_1$, when maximum histamine-induced contraction has been produced, give, respectively, relaxant activities (PD$_2$) of 7.65 ± 0.43 and 5.54 ± 0.46, respectively, calculated according to the method of Rossum et al [Arch. Int. Pharmacodyn. Ther., 143, 299 (1963)], the PD$_2$ value being the negative logarithm of the gram concentration of the compound producing 50% relaxation of the tracheal muscle, in 5 out of 5 preparations each, i.e. 16-methylene-PGE$_1$ methyl ester and 16-methylene-13,14-dihydro-15(ξ)-PGE$_1$ produce, respectively, 50% relaxation of histamine-induced contraction in 5 out of 5 preparations each at doses of $10^{-7.65}$ and $10^{-5.54}$ g./ml., respectively. The prostaglandin analogues of general formula IV, and cyclodextrin clathrates and non-toxic salts thereof, exhibit the aforesaid valuable properties at doses which do not, in general, induce diarrhoea. For example, the doses of 16-methylene-PGE$_1$ methyl ester and 16-methylene-13,14-dihydro-15(ξ)-PGE$_1$ required to produce wet faeces in 50% of mice by oral administration are 0.34 and 0.88 mg./kg. animal body weight, respectively. The coronary vasodilator properties and inhibitory activity on blood platelet aggregation of the prostaglandin analogues of general formula IV are particularly remarkable, for example, 16-methylene-PGE$_1$ methyl ester and 16-methylene-13,14-dihydro-15(ξ)-PGE$_1$ are 100 times and 6 times, respectively, more potent than their closely related congener 16-methylene-PGE$_2$ methyl ester as coronary vasodilators in the rabbit isolated heart, and 180 times and 10 times, respectively, more potent than 16-methylene-PGE$_2$ methyl ester in producing 50% inhibition of adenosine diphosphate-induced blood platelet aggregation in platelet-rich plasma of rats.

The prostaglandin analogues of general formula IV, and cyclodextrin clathrates and non-toxic salts thereof, induce moderate cutaneous inflammation upon topical application to the skin. This topical activity may be indicated in the management of chronically recurrent skin diseases which may respond to induced inflammation, e.g. psoriasis.

According to a feature of the present invention, the prostaglandin analogues of general formula IV wherein A represents a grouping of formula II, $R^1$ and X are as hereinbefore defined and $R^2$ represents a hydrogen atom or an alkyl group containing from 1 to 4 carbon atoms, i.e. a compound of the general formula:

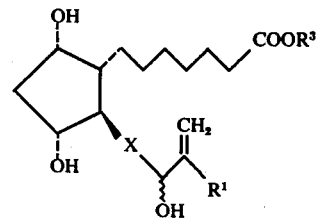

V (wherein $R^3$ represents a hydrogen atom or a straight- or branched-chain alkyl group containing from 1 to 4 carbon atoms, and $R^1$ and X are as hereinbefore defined) are prepared by the process which comprises the hydrolysis under alkaline conditions of a compound of the general formula:

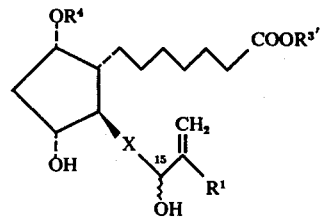

VI wherein $R^{3'}$ represents a straight- or branched-chain alkyl group containing from 1 to 4 carbon atoms, $R^4$ represents an alkylcarbonyl group, preferably containing from 2 to 4 carbon atoms, e.g. acetyl, and $R^1$ and X are as hereinbefore defined. The hydrolysis under alkaline conditions may be effected with potassium carbonate in an anhydrous alkanol containing from 1 to 4 carbon atoms, preferably absolute methanol, at a temperature ranging from ambient to 45° C., and preferably for a period of 30 to 60 minutes, to give compounds of general formula V wherein $R^3$ represents an alkyl group, or under more vigorous conditions, for example with an aqueous solution of an alkali metal, e.g. sodium or potassium, hydroxide or carbonate in the presence of an organic solvent miscible with water, e.g. an alkanol containing from 1 to 4 carbon atoms or tetrahydrofuran, to give compounds of general formula V wherein $R^3$ represents a hydrogen atom.

Prostaglandin analogues of general formula IV wherein A represents a grouping of formula II, $R^1$ and X are as hereinbefore defined and $R^2$ represents a hydrogen atom, obtained by the aforementioned process may be esterified to give corresponding compounds wherein $R^2$ represents an alkyl group by reaction of the acids with (i) diazoalkane compounds, e.g. diazomethane, (ii) alcohols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Patents Nos. 1362956 and 1364125).

According to a further feature of the present invention, the prostaglandin analogues of general formula IV wherein A represents a grouping of formula III, $R^1$ and X are as hereinbefore defined and $R^2$ represents a hydrogen atom or an alkyl group containing from 1 to 12 carbon atoms, are prepared by the process which comprises hydrolyzing the trimethylsilyloxy groups of a compound of the general formula:

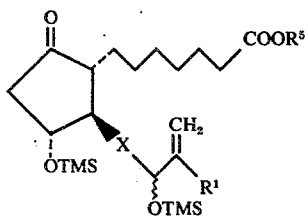

VII (wherein $R^1$ and X are as hereinbefore defined, $R^5$ represents a straight- or branched-chain alkyl group containing from 1 to 12 carbon atoms, and TMS represents the trimethylsilyl group) to hydroxy groups under extremely mild acidic conditions, for example by treatment with an aqueous oxalic acid solution in the presence of an inert organic solvent, e.g. ethyl acetate, to give a compound of the general formula:

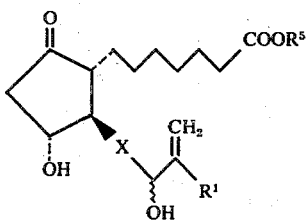

VIII (wherein $R^1$, X and $R^5$ are as hereinbefore defined), followed, if desired, by treatment of the ester with baker's yeast [cf. C.J. Sih et al, J. Amer. Chem. Soc. 94, 3643-3644 (1972)] to give a corresponding acid of general formula IV wherein A represents a grouping of formula III and $R^2$ represents a hydrogen atom.

The compounds of general formula VII may be prepared by the oxidation of a compound of the general formula:

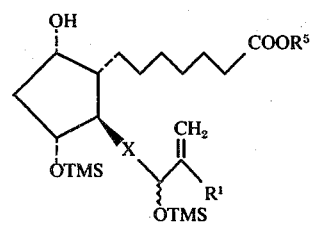

IX (wherein $R^1$, X, $R^5$ and TMS are as herein before defined) with Collin's reagent (chromium trioxide — pyridine complex) in the presence of an inert organic solvent, e.g. methylene chloride, preferably at a temperature of about 10° C., or with dimethylsulphide-N-chlorosuccinimide at 0° C. to −30° C. [cf. E. J. Corey and C. U. Kim, J. Amer. Chem. Soc. 94, 7586 (1972)].

The compounds of general formula IX may be prepared by the reaction of a compound of the general formula:

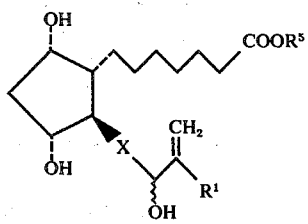

X (wherein $R^1$, X and $R^5$ are as hereinbefore defined) with N-trimethylsilyldiethylamine or N,O-bis(trimethylsilyl)-acetamide in acetone, preferably at a temperature of about 30° C.

The hereinbefore described sequence of reactions is illustrated schematically in following Chart A, wherein X, $R^1$, $R^3$, $R^3{}'$ $R^4$ and $R^5$ are as hereinbefore defined.

CHART A

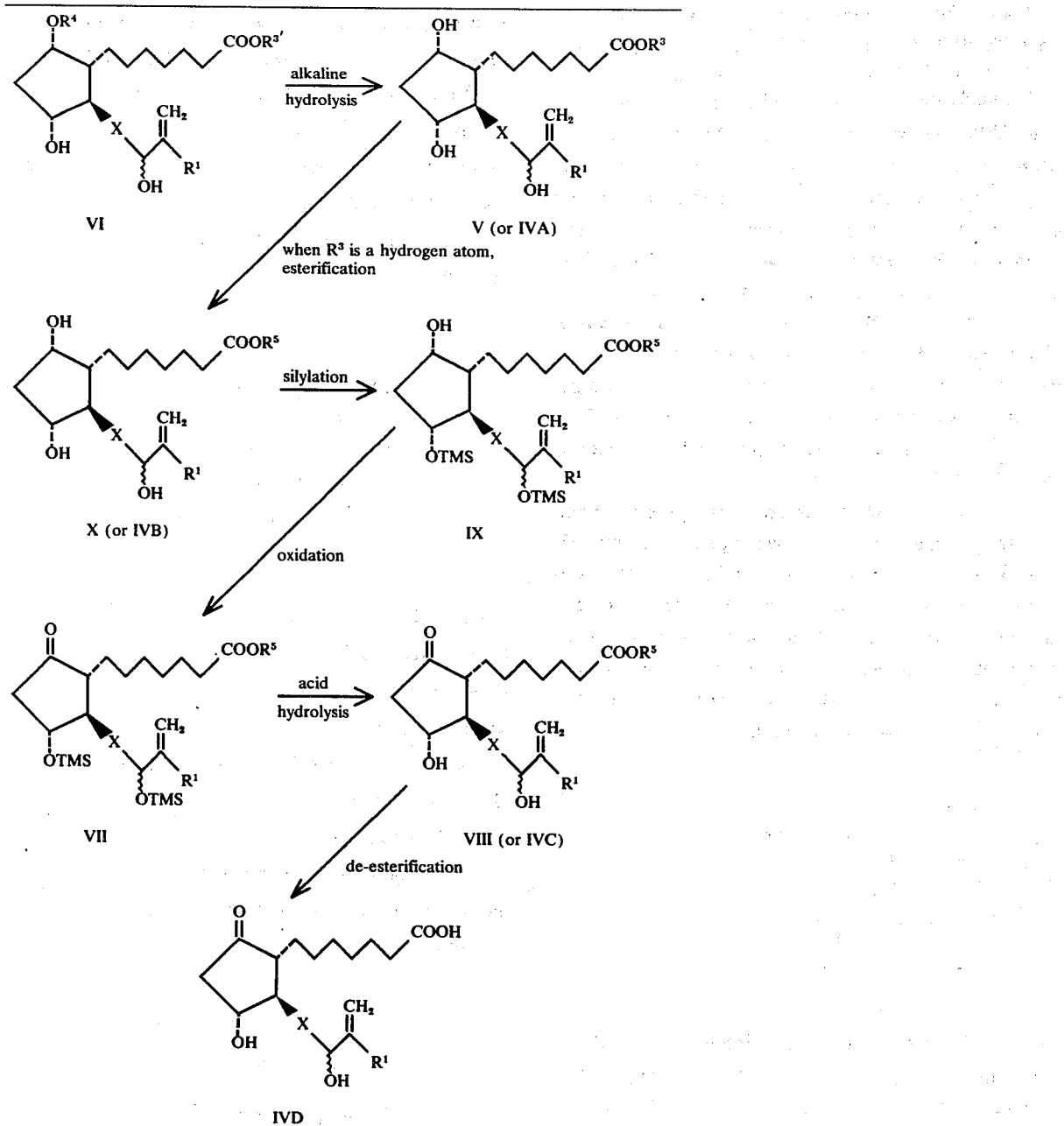

Compounds of general formula VI wherein X represents ethylene and the other symbols are as hereinbefore defined, used as starting materials in the aforedescribed process, may be obtained from a compound of the general formula:

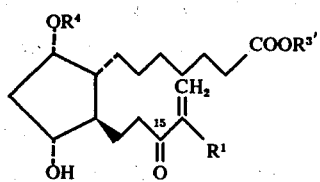

XI (wherein $R^1$, $R^{3'}$ and $R^4$ are as hereinbefore defined) by reducing the oxo group to a hydroxy group. The reduction is suitably effected with excess sodium borohydride in an alkanol containing from 1 to 4 carbon atoms, e.g. methanol, at a low temperature, preferably at $-30°$ to $-60°$ C. The product thus obtained is a mixture of isomers of formula IV in which the hydroxy group at position 15 is in $\alpha$- or $\beta$-configuration. If desired, the isomer having the hydroxy group in $\alpha$-configuration may be separated from the isomer having the hydroxy group in $\beta$-configuration by column chromatography of the mixture on silica gel.

Compounds of general formula VI, wherein X represents trans-vinylene and the other symbols are as hereinbefore defined, may be obtained by the reduction of a compound of the general formula:

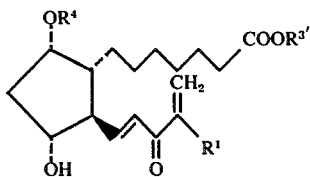

(wherein $R^1$, $R^{3'}$ and $R^4$ are as hereinbefore defined) by treatment with excess sodium borohydride in an alkanol containing from 1 to 4 carbon atoms, e.g. methanol, at a temperature of −40° to −30° C. for one hour. The product thus obtained is a mixture of isomers of formula VI in which X represents trans-vinylene and the hydroxy group at position 15 is in α- or β-configuration, and a compound of general formula XI wherein $R^1$, $R^{3'}$ and $R^4$ are as hereinbefore defined.

Compounds of general formula XII wherein $R^1$, $R^{3'}$ and $R^4$ are as hereinbefore defined, may be obtained from a compound of the general formula:

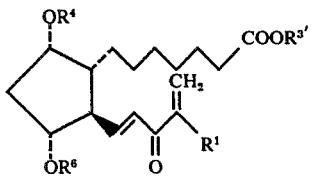

(wherein $R^6$ represents a 2-tetrahydropyranyl group unsubstituted or substituted by at least one alkyl group, or a 2-tetrahydrofuranyl or 1-ethoxyethyl group, and the other symbols are as hereinbefore defined) by mild hydrolysis with an aqueous solution of an organic acid, e.g. acetic acid or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60° C.

Compounds of general formula XIII, wherein $R^1$, $R^{3'}$, $R^4$ and $R^6$ are as hereinbefore defined, may be obtained by the Wittig reaction of a compound of the general formula:

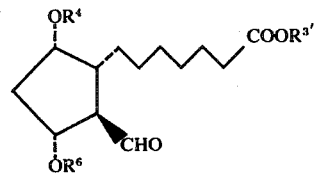

(wherein $R^{3'}$, $R^4$ and $R^6$ are as hereinbefore defined) with the sodio derivative of a compound of the general formula:

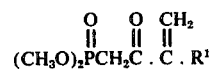

wherein $R^1$ is as hereinbefore defined. The reaction is preferably effected by suspending sodium hydride in an inert organic medium, e.g. tetrahydrofuran or 1,2-dimethoxyethane, and adding the dimethyl phosphonate of formula XV. The resulting sodio derivative of the dimethyl phosphonate is then reacted with the compound of formula XIV at 20° to 40° C. for 2 hours to form stereospecifically the trans-enone compound of formula XIII.

The dimethy phosphonates of formula XV may be prepared as described in U.S. Pat. Ser. No. 3,953,495.

The compounds of general formula XIV, wherein $R^{3'}$, $R^4$ and $R^6$ are as hereinbefore defined, used as starting materials in the hereinbefore described procedures, may themselves be prepared by methods known per se from compounds of general formula XVI depicted hereafter by the series of reactions depicted schematically below in Chart B, wherein $R^{3'}$, $R^4$ and $R^6$ are as hereinbefore defined and Y represents cis-vinylene or ethylene.

CHART B

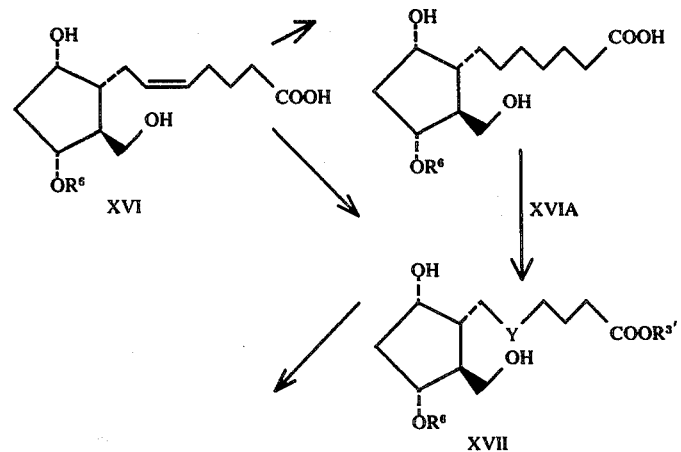

CHART B-continued

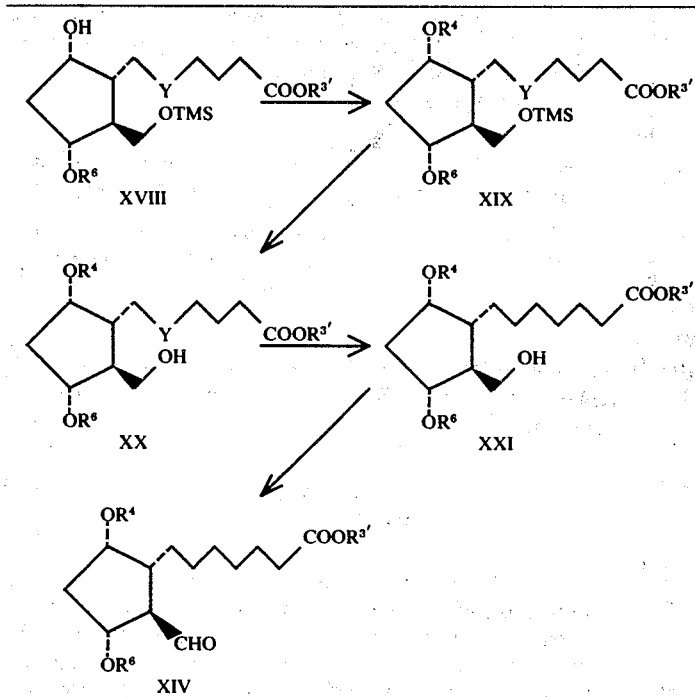

Compounds of formula XVI, if desired, may be reduced to give compounds of formula XVIA. Suitably the reduction of compounds of formula XVI may be effected by hydrogenation in the presence of a hydrogenation catalyst, for example palladium on charcoal, palladium black or platinum oxide, in the presence of an inert organic solvent, for example an alkanol containing from 1 to 4 carbon atoms, e.g. methanol or ethanol, at laboratory temperature at normal or elevated pressure, e.g. at a hydrogen pressure from atmospheric to 15 kilogrammes per square centimeter. Compounds of formulae XVI or XVIA are esterified by, for example, reaction with a diazoalkane containing from 1 to 4 carbon atoms, e.g. diazomethane, in a suitable inert organic solvent, e.g. diethyl ether, to give esters of formula XVII. Compounds of formula XVIII are prepared by reacting a compound of formula XVII with trimethylchlorosilane in an inert organic solvent, for example methylene chloride, in the presence of a base, for example pyridine or a tertiary amine, at a low temperature, e.g. at a temperature of −30° C. to 0° C. Compounds of formula XIX are prepared by reacting a trimethylsilyl ether of formula XVIII with the appropriate acyl chloride or acid anhydride in an inert organic solvent, for example methylene chloride, in the presence of a base, for example pyridine or a tertiary amine, at a low temperature, e.g. at a temperature of 0° to 30° C. Compounds of formula XX are prepared by treating a compound of formula XIX by methods known per se for the removal of the trimethylsilyl group, for example by treatment with an acid; it is preferable not to use a strong acid in order to avoid the risk of removal of the group $R^6$. Compounds of formula XX, wherein Y represents cis-vinylene and the other symbols are as hereinbefore defined, are reduced to give compounds of formula XXI. Suitably, the reduction may be effected by hydrogenation in the presence of a hydrogenation catalyst as hereinbefore described for the reduction of compounds of formula XVI to compounds of formula XVIA. Compounds of formula XXI are converted to compounds of formula XIV under mild and neutral conditions, for example with chromium trioxide-pyridine complex or Jones' reagent and at a moderately low temperature.

The processes hereinbefore described for the preparation of compounds of general formula VI may be represented by the series of reactions depicted schematically below in Chart C, wherein the various symbols are as hereinbefore defined.

CHART C

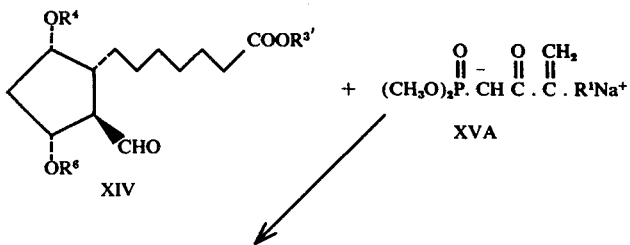

CHART C-continued

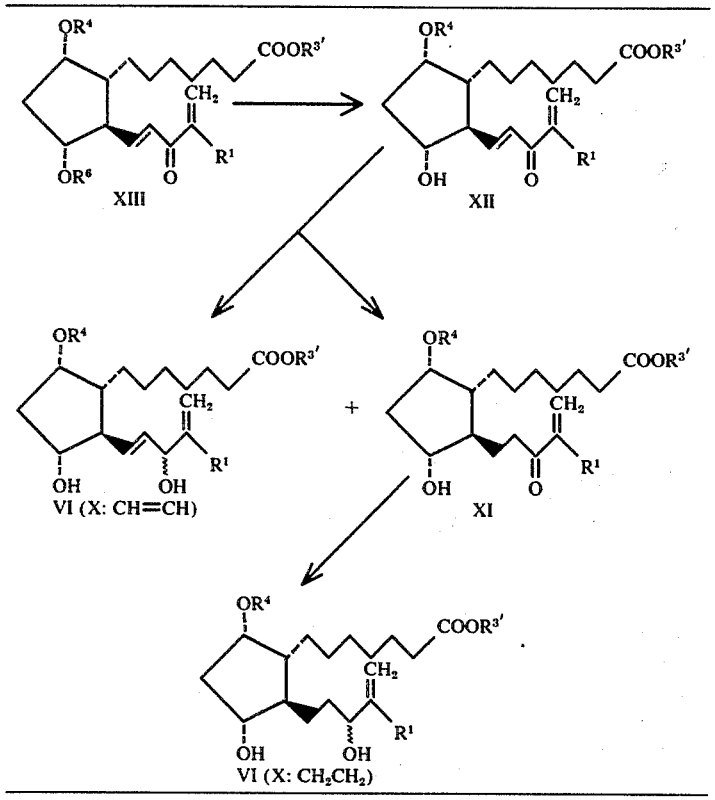

The compounds of formula XVI (cf. Chart B) may themselves be prepared by methods known per se from the known compounds of formula XXII below [the racemic form of the compound of formula XXII is described in J. Amer. Chem. Soc., 91, 5675 (1969) and the natural configuration compound of formula XXII is described in J. Amer. Chem. Soc., 92, 397 (1970)] which may be represented by the series of reactions depicted schematically below in Chart D.

CHART D

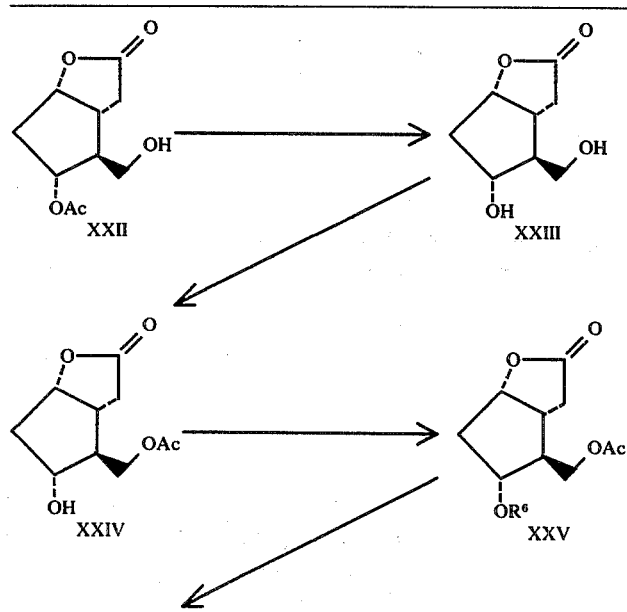

CHART D-continued

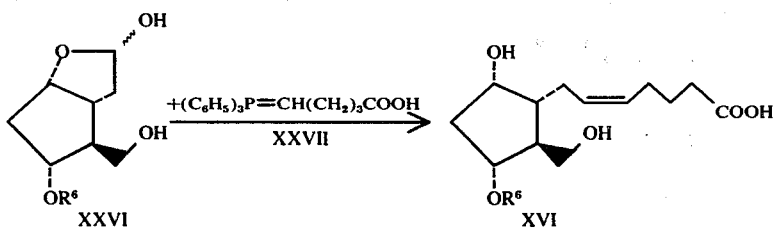

wherein Ac represents the acetyl group and $R^6$ is as hereinbefore defined.

Compounds of formula XXIII may be prepared by hydrolysis under alkaline conditions of compounds of formula XXII. Compounds of formula XXIV may be obtained by the acetylation of compounds of formula XXIII under mild conditions and may be converted into compounds of formula XXV by reaction with a dihydropyran, dihydrofuran or ethyl vinyl ether in an inert solvent, e.g. methylene chloride, in the presence of a condensing agent, e.g. p-toluenesulphonic acid. Compounds of formula XXVI may be prepared by reducing compounds of formula XXV with diisobutylaluminium hydride in toluene for about 15 minutes at −60° C. Dimsyl anion, previously prepared from sodium hydride and dimethyl sulphoxide, is reacted with 4-carboxy-n-butyltriphenylphosphonium bromide to form 4-carboxy-n-butylidenetriphenylphosphorane of formula XXVII. To that compound is added a compound of formula XXVI and the mixture in dimethyl sulphoxide is made to react for 2 hours at room temperature to yield a compound of formula XVI.

According to another feature of the present invention, the prostaglandin analogues of general formula IV wherein A represents a grouping of formula III, $R^1$ is as hereinbefore defined, $R^2$ represents a hydrogen atom and X represents ethylene, i.e. compounds of the general formula:

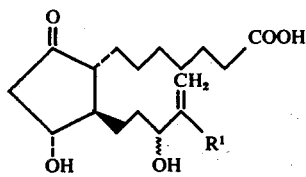

(wherein $R^1$ is as hereinbefore defined) are prepared from a compound of the general formula:

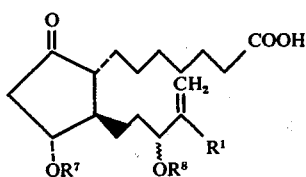

(wherein $R^1$ is as hereinbefore defined, and $R^7$ and $R^8$ each represent a 2-tetrahydropyranyl group unsubstituted or substituted by at least one alkyl group, or a 2-tetrahydrofuranyl or 1-ethoxyethyl group) by mild hydrolysis with an aqueous solution of an organic or inorganic acid under the same reaction conditions as are used for the conversion of compounds of general formula XIII to compounds of general formula XII as hereinbefore described.

The compounds of general formula XXIX may be prepared by the oxidation of a compound of the general formula:

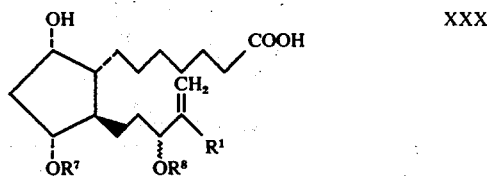

(wherein the various symbols are as hereinbefore defined) with Jones' reagent or with the same reagents as are used for oxidation of compounds of general formula IX to compounds of general formula VII, or with a chromic acid solution, e.g. obtained from chromium trioxide, manganese sulphate, sulphuric acid and water.

The compounds of general formula XXX may be prepared by hydrolysis of a compound of the general formula:

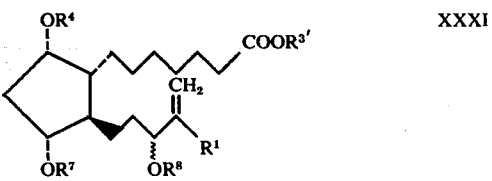

(wherein the various symbols are as hereinbefore defined) with an aqueous solution of an alkali metal, e.g. sodium or potassium, hydroxide or carbonate in the presence of an organic solvent miscible with water, e.g. an alkanol containing from 1 to 4 carbon atoms or tetrahydrofuran.

The compounds of general formula XXXI may be prepared by reacting a compound of general formula VI, wherein X represents ethylene and the other symbols are as hereinbefore defined, with a dihydropyran, dihydrofuran or ethyl vinyl ether in an inert organic solvent, e.g. methylene chloride, in the presence of a condensing agent, e.g. p-toluenesulphonic acid.

The hereinbefore described sequence of reactions is illustrated schematically in following Chart E wherein the various symbols are as hereinbefore defined.

CHART E

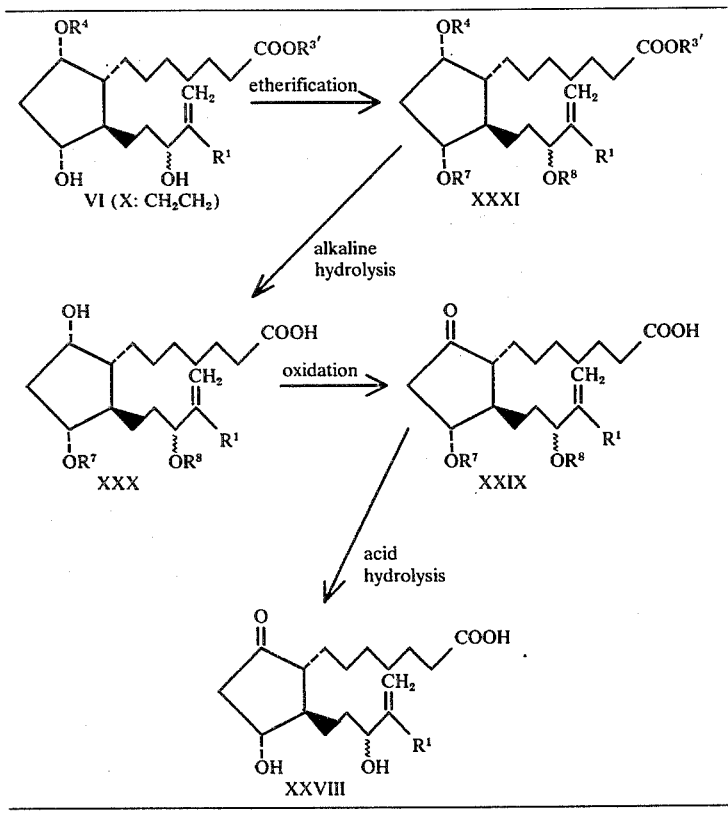

Prostaglandin analogues of general formula IV wherein A represents a grouping of formula III, $R^1$ and X are as hereinbefore defined, and $R^2$ represents a straight- or branched-chain alkyl group containing from 1 to 12 carbon atoms, may be prepared by esterification of corresponding acids of formula IV wherein $R^2$ represents a hydrogen atom (cf. formula IVD) by methods hereinbefore mentioned for the esterification of prostaglandin analogues of general formula IV wherein A represents a grouping of formula II.

Compounds of general formula IV wherein $R^2$ represents a hydrogen atom may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula IV are not vitiated by side-effects ascribable to those cations. Preferably the salts are water-soluble. Suitable salts include the alkali metal, e.g. sodium and potassium, and ammonium salts and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from compounds of general formula IV wherein $R^2$ represents a hydrogen atom by methods known per se, for example by reaction of stoichiometric quantities of compounds of general formula IV and the appropriate base, e.g. an alkali metal hydroxide or carbonate, ammonium hydroxide, ammonia or an amine, in a suitable solvent. The salts may be isolated by lyophilisation of the solution or, if sufficiently insoluble in the reaction medium, by filtration, if necessary after removal of part of the solvent.

Cyclodextrin clathrates of compounds of general formula IV may be prepared by dissolving the cyclodextrin in water and/or an organic solvent which is miscible with water and adding to the solution the compound of general formula IV in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. α-, - or γ-Cyclodextrins or mixtures thereof may be used in the preparation of the cyclodextrin clathrates. Conversion into their cyclodextrin clathrates serves to increase the stability of the compounds of general formula IV.

By the term 'methods known per se' as used in the present specification is meant methods heretofore used or described in the chemical literature.

The compounds of general formulae VI, VII, IX, XXIX, XXX and XXXI employed as starting materials for the preparation of the prostaglandin analogues of general formula IV are themselves new and, as such, constitute a further feature of the invention.

The following Reference Examples and Examples illustrate the preparation of the new prostaglandin analogues of general formula IV. In the Examples 'IR', 'NMR' and 'TLC' represent, respectively, 'Infrared absorption spectrum', 'Nuclear magnetic resonance spectrum' and 'Thin layer chromatography'.

REFERENCE EXAMPLE 1

2α-(6-Methoxycarbonylhex-cis-2-enyl)-3β-hydroxymethyl-4α-(2-tetrahydropyranyloxy)-cyclopentan-1α-ol To a solution of 18.8 g. of 2α-(6-carboxyhex-cis-2-enyl)-3β-hydroxymethyl-4α-(2-tetrahydropyranyloxy)-cyclopentan-1α-ol in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a cyclohexaneethyl acetate mixture (2:1) as eluent to give 15.4 g. of the title compound as a colourless oil having the following physical characteristics:

IR (liquid film): λ; 3450, 2950, −2870, 1740, 1440, 1360, 1325, 1250, 1200, 1140, 1120, 1080, 1025 cm$^{-1}$;

NMR (in CDCl$_3$ solution): δ; 5.55–5.00 (2H, m), 4.78–4.30 (1H, m), 4.20–3.06 (6H, m), 3.55 (3H, s) and 2.97 (2H, s); TLC (developing solvent methylene chloride:methanol = 19:1); Rf = 0.43.

2α-(6-Carboxyhex-cis-2-enyl)-3β-hydroxymethyl-4α-(2-tetrahydropyranyloxy)-cyclopentan-1α-ol, used as starting material in the above procedure, was prepared from 2-oxa-3-oxo-6-syn-hydroxymethyl-7-anti-acetoxy-cis-bicyclo[3,3,0]octane[prepared as described by E. J. Corey et al, J. Amer. Chem. Soc., 92, 397, (1970)] as follows:

190 g. of 2-oxa-3-oxo-6-syn-hydroxymethyl-7-anti-acetoxy-cis-bicyclo[3,3,0]octane in 1.5 liters of absolute methanol and 130 g. of potassium hydroxide were stirred at room temperature for one hour, and then successively cooled in an ice-bath, and neutralized with hydrochloric acid. The precipitate was filtered off and the filtrate was concentrated under reduced pressure. The residue was washed with ethanol, and then with ethyl acetate, and dried to give 124 g. of 2-oxa-3-oxo-6-synhydroxymethyl-7-anti-hydroxy-cis-bicyclo[3,3,-0]octane as white crystallites having the following physical characteristics:

m.p.; 119° C.;

IR (KBr tablet): ν 3350, 2970–2880, 1740, 1480, 1440, 1410, 1380, 1335, 1305, 1270, 1205, 1100, 1080, 1060, 1040, 1020, 1000, 975 cm$^{-1}$;

NMR (in CDCl$_3$ + deutero dimethyl sulphoxide solution): δ; 5.10–4.60 (1H, m), 4.29 (2H, s), 4.13–3.77 (1H, m) and 3.38 (2H, d);

TLC (developing solvent methylene chloride:methanol = 20:1);
Rf = 0.27.

124 g. of 2-oxa-3-oxo-6-syn-hydroxymethyl-7-antihydroxy-cis-bicyclo[3,3,0]octane, obtained as described above, were dissolved in absolute pyridine (1.4 liters) and cooled to −40° C. 74 g. of acetic anhydride were added dropwise and the mixture stirred for 5 hours at −40° C. to −20° C. and then for 16 hours at 0° C. The pyridine was evaporated off under reduced pressure and the residue was dissolved in 1 liter of ethyl acetate. 200 g. of sodium bisulphate were added, and the mixture stirred vigorously and filtered. The filtrate was concentrated under reduced pressure and the residue was purified by column chromatography on silica gel using a benzene-ethyl acetate mixture (1:3) as eluent to give 112 g. of 2-oxa-3-oxo-6-syn-acetoxy-methyl-7-anti-hydroxy-cis-bicyclo[3,3,0]octane as colourless needles having the following physical characteristics:

m.p.; 36° to 37° C.;

IR (KBr tablet): ν; 3450, 2960, 2850, 1775, 1740, 1420, 1370, 1250, 1190, 1120, 1090, 1040, 980 cm$^{-1}$;

NMR (in CDCl$_3$ solution): δ; 5.15–4.60 (1H, m), 4.3–3.75 (3H, m), 3.50 (1H, s) and 2.02 (3H, s);

TLC (developing solvent methylene chloride:methanol = 20:1);
Rf = 0.50.

4.3 g. of 2-oxa-3-oxo-6-syn-acetoxymethyl-7-anti-hydroxy-cis-bicyclo[3,3,0]octane, obtained as described above, were dissolved in 520 ml. of methylene chloride, 25 g. of dihydropyran and 0.52 g. of p-toluenesulphonic acid were added and the mixture stirred for 20 minutes at room temperature. The reaction mixture was neutralized with an aqueous solution of sodium bicarbonate, diluted with ethyl acetate, washed with water, dried and concentrated under reduced pressure to give 56 g. of 2-oxa-3-oxo-6-syn-acetoxymethyl-7-anti-(2-tetrahydropyranyloxy)-cis-bicyclo[3,3,0]octane as a colourless oil having the following physical characteristics:

IR (liquid film): ν; 2950–2840, 1775, 1740, 1465, 1440, 1390–1340, 1240, 1180, 1140–1120, 1080, 1040, 980 cm$^{-1}$;

NMR (CDCl$_3$ solution): δ; 5.2–4.72 (1H, m), 4.72–4.30 (1H, m), 4.2–3.2 (5H, m), and 2.01 (3H, s);

TLC (developing solvent methylene chloride:methanol = 20:1);
Rf = 0.74.

56 g. of the acetyl ether, prepared as described above, were dissolved in 900 ml. of toluene and cooled to −60° C. 456 ml. of a 25(w/v)% toluene solution of diisobutylaluminium hydride were added and the reaction mixture was stirred for 20 minutes at the same temperature; methanol was added in order to decompose the excess of diisobutylaluminium hydride and water was added. The resulting precipitate was filtered off and the filtrate was dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film): ν; 3400, 2940–2860, 1465–1440, 1380, 1355, 1325, 1260, 1200, 1140, 1120, 1075, 1020 cm$^{-1}$;

TLC (developing solvent ethyl acetate); Rf = 0.25.

37.6 g. of sodium hydride (content 63.5%) were suspended in 400 ml. of dimethyl sulphoxide and stirred at 70° C. for 1.5 hours to obtain sodiomethylsulphinylcarbanide. The reaction mixture was allowed to cool to room temperature and then added dropwise to a solution of 226 g. of 4-carboxy-n-butyltriphenylphosphonium bromide in 460 ml. of dimethyl sulphoxide, the reaction temperature being kept within the range 20° to 25° C.

A solution of 35.2 g. of 2-oxa-3-hydroxy-6-synhydroxymethyl-7-anti-(2-tetrahydropyranyloxy)-cis-bicyclo[3,3,0]octane, prepared as described above, in 90 ml. of dimethyl sulphoxide was added to the above reaction mixture and stirred at 35° to 40° C. for 1.5 hours. The reaction mixture was then poured into 6 liters of ice-water and the neutral substances were removed by extraction with an ethyl acetate-diethyl ether mixture (1:1). The aqueous layer was acidified to pH 2 with a saturated aqueous oxalic acid solution and extracted with a diethyl ether-n-pentane mixture (1:1). The organic layer was washed with water, dried over sodium sulphate and concentrated under reduced pressure. The residue was subjected to column chromatography on silica gel using a benzene-methanol mixture (10:1) as eluent to give 35 g. of 2α-(6-carboxyhex-cis-2-enyl)-3β-hydroxymethyl-4α-(2-tetrahydropyranyloxy)-cyclopentan-1α-ol as a colourless oil having the following physical characteristics:-

IR (liquid film): ν; 3400, 2940, −2860, −2300, 1710, 1450, 1435, 1400, 1355, 1245, 1200, 1140, 1120, 1075, 1025 cm$^{-1}$;

NMR (in CDCl$_3$ solution): ; 6.20 (3H, s), 5.50–5.10 (2H, m), 4.75–4.36 (1H, m), 4.24–3.85 (2H, m) and 3.85–3.0 (4H, m);

TLC (developing solvent chloroform:tetrahydrofuran:acetic acid = 10:2:1); Rf = 0.53.

REFERENCE EXAMPLE 2

1α-Acetoxy-2β-(6-methoxycarbonylhex-cis-2-enyl)-3β-hydroxymethyl-4α-(2-tetrahydropyranyloxy)-cyclopentane 13.1 g. of 2α-(6-methoxycarbonylhex-cis-2-enyl)-3β-hydroxymethyl-4α-(2-tetrahydropyranyloxy)-cyclopentan-1α-ol (prepared as described in Reference Example 1) were dissolved in 250 ml. of absolute methylene chloride, and 25 ml. of pyridine were added. The air in the apparatus was replaced with nitrogen and the contents cooled to −20° C. To the reaction mixture was added dropwise a solution of 5.1 ml. of trimethylchlorosilane in 30 ml. of methylene chloride with stirring and stirred at the same temperature for 30 minutes. A sample of the product thus obtained had the following physical characteristics:

TLC (developing solvent benzene:ethyl acetate = 2:1);
Rf = 0.61.

A solution of 2.9 ml. of acetyl chloride in 20 ml. of methylene chloride was added dropwise to the above reaction mixture and stirred at room temperature for 30 minutes. Then 2 ml. of ethanol were added to decompose the excess of acetyl chloride. Pyridine in the reaction mixture was neutralized by the addition of 50 g. of sodium bisulphate, and the resulting precipitate was filtered off. The filtrate was concentrated under reduced pressure to give a residue having the following physical characteristic:

TLC (developing solvent benzene:ethyl acetate = 2:1);
Rf = 0.82.

The residue was dissolved in 300 ml. of ethyl acetate, 100 ml. of saturated aqueous oxalic acid solution were added and the mixture was stirred vigorously at room temperature. The organic layer was separated, washed successively with water, aqueous sodium bisulphate solution, water and an aqueous solution of sodium chloride, dried with sodium sulphate and concentrated under reduced pressure to give 13.7 g. of crude product. The crude product was subjected to column chromatography on silica gel using a benzene-ethyl acetate mixture (3:1) as eluent to give 7.45 g. of 1α-acetoxy-2α-(6-methoxy-carbonylhex-cis-2-enyl)-3β-hydroxymethyl-4α-(2-tetrahydropyranyloxy)-cyclopentane, 2.40 g. of 1α-hydroxy-2α-(6-methoxycarbonylhex-cis-2-enyl)-3β-hydroxymethyl-4α-(2-tetrahydropyranyloxy)-cyclopentane, 720 mg. of 1α-hydroxy-2α-(6-methoxycarbonylhex-cis-2-enyl)-3β-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α-(2-tetrahydropyranyloxy)-cyclopentane.

1α-Acetoxy-2α-(6-methoxycarbonylhex-cis-2-enyl)-3β-hydroxymethyl-4α-(2-tetrahydropyranyloxy)-cyclopentane had the following physical characteristics:

IR (liquid film): ν; 3450, 3000, 2950, 2870, 1740, 1440, 1380, 1330, 1250, 1200, 1160, 1140, 1080, 1030, 980, 920, 875, 815 cm$^{-1}$;

NMR (in CDCl$_3$ solution): δ; 5.45–5.27 (2H, m), 5.16–4.92 (1H, m), 4.76–4.46 (1H, m), 4.27–3.96 (1H, m), 3.67 (3H, s), 2.98–2.64 (1H, m) and 2.05 (3H, s);

TLC (developing solvent benzene:ethyl acetate = 2:1);
Rf = 0.27.

REFERENCE EXAMPLE 3

1α-Acetoxy-2α-(6-methoxycarbonylhexyl)-3β-hydroxymethyl-4α-(2-tetrahydropyranyloxy)-cyclopentane 1.5 g. of 5% palladium on charcoal were added to a solution of 6.1 g. of 1α-acetoxy-2α-(6-methoxy-carbonylhex-cis-2-enyl)-3β-hydroxymethyl-4α-(2-tetrahydropyranyloxy)-cyclopentane (prepared as described in Reference Example 2) in 150 ml. of methanol. After stirring for 3 hours at room temperature under a hydrogen atmosphere, the reaction mixture was filtered and the palladium on charcoal was washed with methanol. The filtrate and washing were concentrated under reduced pressure to give 6.32 g. of the title compound having the following physical characteristics:

TLC (developing solvent ethyl acetate:benzene = 1:2);
Rf = 0.35;
NMR (CDCl$_3$ solution): δ; 5.20–4.80 (1H, m), 4.80–4.40 (1H, m), 3.70 (3H, s) and 2.05 (3H, s).

REFERENCE EXAMPLE 3A

1α-Acetoxy-2α-(6-methoxycarbonylhexyl)-3β-formyl-4α-(2- tetrahydropyranyloxy)-cyclopentane 18.4 g. of chromium trioxide were added to a stirred solution of 31 ml. of dry pyridine in 400 ml. of dry methylene chloride under an atmosphere of nitrogen. The reaction mixture was stirred for 15 minutes at room temperature, and then 80 g. of infusorial earth were added and the reaction mixture was cooled to 0° C. A solution of 6.32 g. of 1α-acetoxy-2α-(6-methoxycarbonylhexyl)-3β-hydroxymethyl-4α-(2-tetrahydropyranyloxy)-cyclopentane (prepared as described in Reference Example 3) in 100 ml. of dry methylene chloride was added in one portion to the reaction mixture. After stirring an additional 15 minutes at 0° C., 200 g. of sodium bisulphate monohydrate were added, and the mixture was stirred for 10 minutes and filtered over a pad of magnesium sulphate. The filtrate was concentrated under reduced pressure and the residue purified by column chromatography on silica gel using a mixture of ethyl acetate and benzene (1:5) as eluent to give 4.7 g. of the title compound having the following physical characteristics:

TLC (developing solvent ethyl acetate:benzene = 1:2);
Rf = 0.73;
IR (liquid film): ν; 1740, 1440, 1380, 1250, 1140, 1080, 1030, 970, 910, 870, 820 cm$^{-1}$;

NMR (CDCl$_3$ solution): δ; 9.90–9.70 (1H, m), 5.30–5.00 (1H, m), 4.80–4.20 (2H, m), 3.70 (3H, s) and 2.05 (3H, s).

REFERENCE EXAMPLE 4

Methyl 9α-acetoxy-11α-(2-tetrahydropyranyloxy)-15-oxo-16-methyleneprost-trans-13-enoate 624 mg. of sodium hydride (63% content) were suspended in 100 ml. of anhydrous tetrahydrofuran. With stirring under an atmosphere of nitrogen, 4.5 g. of dimethyl 2-oxo-3-methylene-n-heptylphosphonate (prepared as described in Reference Example 2 of U.S. Pat. Ser. No. 3,953,495) in 50 ml. of anhydrous tetrahydrofuran were added dropwise to the suspension and the mixture stirred at 10° C. to room temperature for 30 minutes until the solution became clear. 4.7 g. of 1α-acetoxy-2α-(6-methoxycarbonylhexyl)-3β-formyl-4α-(2-tetrahydropyranyloxy)-cyclopentane (prepared as described in Reference Example 3A) in 100 ml. of anhydrous tetrahydrofuran were added and the mixture stirred at room temperature for 1.5 hours and at 40° C. for 30 minutes. The reaction mixture was then neutralized with acetic acid. The mixture was filtered through a pad of silica gel, and the filtrate concentrated under reduced pressure. The residue was purified by column chromatography on silica gel using a mixture of ethyl acetate and benzene (1:20) as eluent to give 4.6 g. of the title compound having the following physical characteristics:

TLC (developing solvent benzene:ethyl acetate = 5:1);
Rf = 0.56;
IR (liquid film): ν; 1740, 1670, 1620, 1440, 1380, 1250, 1030 cm$^{-1}$;
NMR (CDCl$_3$ solution): δ; 6.90–6.60 (2H, m), 5.90 (1H, s), 5.70 (1H, s), 5.30–5.00 (1H, m), 4.70–4.40 (1H, m), 3.65 (3H, s) and 2.05 (3H, s).

REFERENCE EXAMPLE 5

Methyl 9α-acetoxy-11α-hydroxy-15-oxo-16-methyleneprost-trans-13-enoate 4.6 g. of methyl 9α-acetoxy-11α-(2-tetrahydropyranyloxy)-15-oxo-16-methylene-prost-trans-13-enoate (prepared as described in Reference Example 4) were dissolved in a mixture of 5 ml. of tetrahydrofuran and 50 ml. of a 65% acetic acid aqueous solution and the reaction mixture was stirred at 40° C. for 2.5 hours. The reaction mixture was then poured into 500 ml. of ethyl acetate, washed with an aqueous sodium bicarbonate solution, water and an aqueous sodium chloride solution, dried over magnesium sulphate and concentrated under reduced pressure. The residue was purified by column chromatography on silica gel using a mixture of benzene and ethyl acetate (4:1) as eluent to give 3.9 g. of the title compound having the following physical characteristics:

TLC (developing solvent ethyl acetate:benzene = 1:3);
Rf = 0.30;
IR (liquid film): ν; 3400, 1740, 1670, 1620, 1440, 1380, 1250, 990 cm$^{-1}$;
NMR (CDCl$_3$ solution): δ; 6.90–6.60 (2H, m), 6.00 (1H, s), 5.75 (1H, s), 5.30–5.00 (1H, m), 4.50 (1H, s), 4.30–4.00 (1H, m), 3.70 (3H, s), and 2.10 (3H, s).

EXAMPLE 1

Methyl 9α-acetoxy-11α,15α-dihydroxy-16-methyleneprost-trans-13-enoate and methyl 9α-acetoxy-11α-hydroxy-15-oxo-16-methyleneprostanoate To a solution of 3.9 g. of methyl 9α-acetoxy-11α-hydroxy-15-oxo-16-methyleneprost-trans-13-enoate (prepared as described in Reference Example 5) in 50 ml. of methanol there was added dropwise 1.2 g. of sodium borohydride whilst keeping the temperature at −40° C. to −30° C. After 1 hour, the mixture was neutralized with acetic acid and concentrated under reduced pressure. The residue was extracted with ethyl acetate, and the extract was washed with an aqueous sodium bicarbonate solution, water, and an aqueous sodium chloride solution, dried over magnesium sulphate and concentrated under reduced pressure. The residue was purified by column chromatography on silica gel using a mixture of ethyl acetate and benzene (1:2) as eluent to give 923 mg. of methyl 9α-acetoxy-11α,15α-dihydroxy-16-methyleneprost-trans-13-enoate, 1.033 g. of the 15β-hydroxy isomer, and 653 mg. of methyl 9α-acetoxy-11α-hydroxy-15-oxo-16-methyleneprostanoate.

Methyl 9α-acetoxy-11α,15α-dihydroxy-16-methyleneprost-trans-13-enoate showed the following physical characteristics:

TLC (developing solvent methylene chloride:methanol = 19:1);
Rf = 0.30; (15β-hydroxy isomer: Rf = 0.33);
IR (KBr tablet): ν; 3400, 1740, 1710, 1645, 1625, 1440, 1395, 1280, 1030, 995, 905 cm$^{-1}$;
NMR (CDCl$_3$ solution): δ; 5.70–5.40 (2H, m), 5.30–4.90 (1H, m), 5.10 (1H, s), 4.85 (1H, s), 4.60–4.30 (1H, m), 4.10–3.50 (1H, m), 3.65 (3H, s), 3.40–2.90 (2H, broad) and 2.05 (3H, s);
m.p. 55°–57° C. (15β-hydroxy isomer: 49°–51° C.).

Methyl 9α-acetoxy-11α-hydroxy-15-oxo-16-methyleneprostanoate showed the following physical characteristics:

TLC (developing solvent ethyl acetate:benzene 1:2);
Rf = 0.50;
IR (liquid film): ν; 3450, 1740, 1680, 1630, 1440, 1380, 1250, 1040 cm$^{-1}$;
NMR (CDCl$_3$ solution): δ; 6.05 (1H, s), 5.75 (1H, s), 5.30–4.95 (1H, m), 4.20–3.50 (1H, m), 3.65 (3H, s) and 3.30–2.60 (3H, m);
UV (ethanol solution): $\lambda_{max}$ = 222 mμ.

EXAMPLE 2

16-Methylene-prostaglandin $F_{1\alpha}$ methyl ester

A solution of 979 mg. of methyl 9α-acetoxy-11α,15α-dihydroxy-16-methyleneprost-trans-13-enoate (prepared as described in Example 1) in 7 ml. of dry methanol was stirred with 970 mg. of anhydrous potassium carbonate at room temperature for 20 minutes and at 40° C. for 10 minutes. The reaction mixture was then acidified with 15 ml. of 1.0N hydrochloric acid, stirred at room temperature for 10 minutes, and extracted with ethyl acetate. The organic solution was washed with an aqueous sodium bicarbonate solution and an aqueous sodium chloride solution, dried over magnesium sulphate and concentrated under reduced pressure. The residue was purified by column chromatography on silica gel using a mixture of ethyl acetate and benzene (1:1) as eluent to give 879 mg. of the title compound having the following physical characteristics:

TLC (developing solvent ethyl acetate:benzene = 2:1);
Rf = 0.26;
IR (liquid film):$\nu$; 3400, 1740, 1650, 1440, 980, 910 cm$^{-1}$;
NMR (CDCl$_3$ solution): $\delta$; 5.60–5.30 (2H, m), 5.10 (1H, s), 4.85 (1H, s), 4.60–4.30 (1H, m), 4.30–3.80 (1H, m), 3.65 (3H, s) and 3.60 (3H broad).

EXAMPLE 3

11$\alpha$,15$\alpha$-Bis-trimethylsilyloxy-16-methylene-prostaglandin F$_{1\alpha}$ methyl ester 7.6 ml. of N-trimethylsilyldiethylamine were added, under an atmosphere of nitrogen, to a solution of 879 mg. of 16-methylene-prostaglandin F$_{1\alpha}$ methyl ester (prepared as described in Example 2) in 30 ml. of dry acetone and the reaction mixture was stirred for 1.5 hours at room temperature. The reaction mixture was then diluted with toluene and concentrated under reduced pressure to give 1.2 g. of the title compound having the following physical characteristic:

TLC (developing solvent ethyl acetate: cyclohexane = 1:2);
Rf = 0.64.

EXAMPLE 4

11$\alpha$,15$\alpha$-Bis-trimethylsilyloxy-16-methylene-prostaglandin E$_1$ methyl ester 2 ml. of dimethylsulphide were added, under an atmosphere of nitrogen, to a solution of 1.54 g. of N-chlorosuccinimide in 40 ml. of dry toluene and the reaction mixture was cooled to −40° C. There was then added a solution of 1.2 g. of 11$\alpha$,15$\alpha$-bis-trimethylsilyloxy-16-methylene-prostaglandin F$_{1\alpha}$ methyl ester (prepared as described in Example 3) in 40 ml. of dry toluene. After stirring for 2 hours at −40° C., a solution of 2.5 ml. of triethylamine in 4 ml. of dry pentane was added and the reaction mixture was stirred for 10 minutes at room temperature and extracted with diethyl ether. The organic solution was washed with water and concentrated under reduced pressure to give 962 mg. of the title compound having the following physical characteristic:

TLC (developing solvent ethyl acetate:cyclohexane = 1:2);
Rf = 0.74.

EXAMPLE 5

16-Methylene-prostaglandin E$_1$ methyl ester 100 ml. of saturated aqueous oxalic acid solution was added to a solution of 962 mg. of 11$\alpha$,15$\alpha$-bis-trimethylsilyloxy-16-methylene-prostaglandin E$_1$ methyl ester (prepared as described in Example 4) in 500 ml. of ethyl acetate. After stirring for 2 hours at room temperature, the reaction mixture was washed with an aqueous sodium bicarbonate solution, water, and an aqueous sodium chloride solution, dried over magnesium sulphate and concentrated under reduced pressure. The residue was purified by column chromatograhy on silica gel using a mixture of ethyl acetate and cyclohexane (1:2) as eluent to give 239 mg. of the title compound having the following physical characteristics:

TLC (developing solvent ethyl acetate:cyclohexane = 4:1); Rf = 0.43;
IR (liquid film):$\nu$; 3400, 1740, 1650, 1440, 1340, 1170, 1080, 980, 910 cm$^{-1}$;
NMR (CDCl$_3$ solution): $\delta$; 5.80–5.58 (2H, m), 5.20–5.07 (1H, s), 5.00–4.80 (1H, s), 4.65–4.40 (1H, m), 4.20–3.90 (1H, q) and 2.90–2.55 (1H, dd).

EXAMPLE 6

Methyl 9$\alpha$-acetoxy-11$\alpha$,15($\xi$)-dihydroxy-16-methylene-prostanoate To a solution of 918 mg. of methyl 9$\alpha$-acetoxy-11$\alpha$-hydroxy-15-oxo-16-methyleneprostanoate (prepared as described in Example 1) in 10 ml. of methanol there was added dropwise 240 mg. of sodium borohydride whilst keeping the temperature at −40° to −30° C. After 30 minutes, the mixture was neutralized with acetic acid and concentrated under reduced pressure. The residue was extracted with ethyl acetate, and the extract was washed with an aqueous sodium bicarbonate solution and an aqueous sodium chloride solution, dried over magnesium sulphate and concentrated under reduced pressure. The residue was purified by column chromatography on silica gel using a mixture of ethyl acetate and benzene (1:2) as eluent to give 500 mg. of the title compound having the following physical characteristics:

TLC (developing solvent ethyl acetate:benzene = 1:1); Rf = 0.33;
IR (liquid film): $\nu$; 3400, 1740, 1650, 1440, 1380, 1250, 1040, 900 cm$^{-1}$;
NMR (CDCl$_3$ solution): $\delta$; 5.30–4.95 (2H, m), 4.85 (1H, s), 4.20–3.60 (2H, m), 3.70 (3H, s) and 3.35 (2H, s).

EXAMPLE 7

Methyl 9$\alpha$-acetoxy-11$\alpha$,15($\xi$)-bis-(2-tetrahydropyranyloxy)-16-methyleneprostanoate 5 mg. of p-toluenesulphonic acid and 1.0 ml. of 2,3-dihydropyran were added to a solution of 500 mg. of methyl 9$\alpha$-acetoxy-11$\alpha$, 15($\xi$)-dihydroxy-16-methyleneprostanoate (prepared as described in Example 6) in 3 ml. of methylene chloride and the reaction mixture was stirred at room temperature for 15 minutes and then diluted with 100 ml. of ethyl acetate. The mixture was washed with an aqueous sodium bicarbonate solution, water, and an aqueous sodium chloride solution, dried over magnesium sulphate and concentrated under reduced pressure to give 700 mg. of the title compound having the following physical characteristics:

TLC (developing solvent ethyl acetate:benzene = 1:2);
Rf = 0.80;
IR (liquid film): $\nu$; 1740, 1670, 1650, 1630, 1440, 1380, 1360, 1250, 905 cm$^{-1}$;
NMR (CDCl$_3$ solution): $\delta$; 5.20–4.75 (3H, m), 4.75–4.40 (2H, m), 3.65 (3H, s) and 2.05 (3H, s).

EXAMPLE 8

9$\alpha$-Hydroxy-11$\alpha$,15($\xi$)-bis-(2-tetrahydropyranyloxy)-16-methyleneprostanoic acid 700 mg. of methyl 9$\alpha$-acetoxy-11$\alpha$,15($\xi$)-bis-(2-tetrahydropyranyloxy)-16-methyleneprostanoate (prepared as described in Example 7) were dissolved in a mixture of 15 ml. of a 10% potassium hydroxide aqueous solution, 10 ml. of methanol and 5 ml. of tetrahydrofuran, and the solution was stirred at room temperature to 40° C. for one hour. After cooling to room temperature, the reaction mixture was diluted with ethyl acetate, and acidified to pH 5 with an aqueous oxalic acid solution. The organic solution was washed with water and an aqueous sodium chloride solution, dried over magnesium sulphate, and concentrated under reduced pressure to give 630 mg. of the title compound having the following physical characteristics:

TLC (developing solvent ethyl acetate:benzene = 1:1);
Rf = 0.50;
IR (liquid film): $\nu$; 3450, 3500–2500, 1720, 1670, 1650, 1630, 1440, 1380, 1360, 1250, 1130, 1080, 1030, 910, 875, 820 $cm^{-1}$;
NMR ($CDCl_3$ solution): $\delta$; 8.40 (2H, s), 5.20–4.40 (4H, m) and 4.40–3.20 (7H, m).

EXAMPLE 9

9-Oxo-11α,15(ξ)-bis-(2-tetrahydropyranyloxy)-16-methyleneprostanoic acid

To a solution of 630 mg. of 9α-hydroxy-11α,15(ξ)-bis-(2-tetrahydropyranyloxy)-16-methyleneprostanoic acid (prepared as described in Example 8) in 15 ml. of diethyl ether there was added a solution of 0.45 ml. of sulphuric acid, 1.425 g. of manganese sulphate and 0.6 g. of chromium trioxide in 7.5 ml. of water. After stirring for 1 hour at 0° C., the reaction mixture was extracted with ethyl acetate. The organic solution was washed with water and an aqueous sodium chloride solution, dried over magnesium sulphate and concentrated under reduced pressure. The residue was purified by column chromatography on silica gel using a mixture of ethyl acetate and benzene (1:4) as eluent to give 377 mg. of the title compound having the following physical characteristics:

TLC (developing solvent ethyl acetate:benzene = 1:1);
Rf = 0.66;
IR (liquid film):$\nu$; 3500–2500, 1740, 1710, 1640, 1440, 1360, 1200, 1130, 1080, 910, 880, 820 $cm^{-1}$;
NMR ($CDCl_3$ solution): $\delta$; 9.20–8.50 (1H, broad), 5.10–4.40 (4H, m) and 4.30–3.20 (6H, m).

EXAMPLE 10

16-Methylene-13,14-dihydro-15(ξ)-prostaglandin $E_1$ 377 mg. of 9-oxo-11α,15(ξ)-bis-(2-tetrahydropyranyloxy)-16-methyleneprostanoic acid (prepared as described in Example 9) were dissolved in a mixture of 1 ml. of tetrahydrofuran and 10 ml. of a 65% acetic acid aqueous solution, and the reaction mixture was stirred at 40° C. for one hour. The reaction mixture was then extracted with ethyl acetate, and the extract was washed with water and an aqueous sodium chloride solution, dried over magnesium sulphate and concentrated under reduced pressure. The residue was purified by column chromatography on silica gel using a mixture of ethyl acetate and cyclohexane (2:1) as eluent to give 150 mg. of the title compound having the following physical characteristics:

TLC (developing solvent chloroform:tetrahydrofuran:acetic acid = 10:2:1);
Rf = 0.42;
IR (liquid film): $\nu$; 3400, 1750–1710, 1650, 1460, 1250, 1060, 905 $cm^{-1}$;
NMR ($CDCl_3$ solution): $\delta$; 5.30–4.50 (5H, m), 4.30–3.90 (2H, m), 2.90–2.50 (1H, dd) and 1.10–0.70 (3H, t).

The present invention includes within its scope pharmaceutical compositions which comprise at least one new therapeutically useful prostaglandin compound according to the present invention, together with a pharmaceutical carrier or coating. In clinical practice the new compounds of the present invention will normally be administered orally, vaginally, rectally, parenterally or topically.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral adminsitration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses per person are generally between 0.01 and 5 mg. by oral administration in the treatment of hypertension, between 0.5 and 100 $\mu$g. by oral administration in the treatment of gastric ulceration, between 10 and 100 $\mu$g. by aerosol administration in the treatment of asthma, between 0.01 and 5 mg. by oral administration in the treatment of disorders of the peripheral circulation, and between 0.25 and 50 mg. by oral administration in the prevention and treatment of cerebral thrombosis and myocardial infarction.

Prostaglandin compounds according to the present invention may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically acceptable volatile liquid propellants, in conventional pressurized packs which may be made of any suitable material, e.g. metal, plastics or glass, adequate to withstand the pressures generated by the volatile propellant in the pack. Pressurized pharmaceutically acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of the two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg., of active ingredients per ml. of solution or suspension. It is important that the pH of solutions and suspensions used, according to the present invention, to generate aerosols should be kept within the range 3 to 8 and preferable that they should be stored at or below 4° C. to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 11

16-Methylene-13,14-dihydro-15($\xi$)-PGE$_1$ (500 $\mu$g.) was dissolved in ethanol (1 ml.) and the solution obtained was added to an aqueous solution (12 ml.) containing sodium carbonate (50 mg.). Aqueous sodium chloride solution (0.9% w/v, 2 ml.) was then added to give a final volume of 15 ml. The solution was then sterilized by passage through a bacteria-retaining filter and placed in 1.5 ml. portions in 5 ml. ampoules, to give 50 μg. of the prostaglandin analogue (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

EXAMPLE 12

16-Methylene-PGE₁ methyl ester (2 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 μg. of 16-methylene-PGE₁ methyl ester, which after swallowing of the capsules is released into the stomach.

We claim:

1. A compound of the formula:

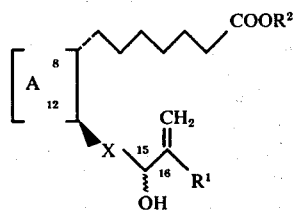

wherein A represents a grouping of the formula:

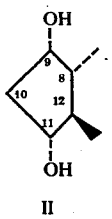 or 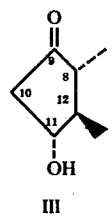

II   III

, $R^1$ represents a hydrogen atom or a straight- or branched-chain alkyl group containing from 1 to 6 carbon atoms, $R^2$ represents a hydrogen atom or a straight- or branched-chain alkyl group containing from 1 to 12 carbon atoms, X represents trans-vinylene or ethylene, and the wavy line indicates attachment of the hydroxy radical in α- or β-configuration and cyclodextrin clathrates thereof and, when $R_2$ represents a hydrogen atom, non-toxic salts thereof.

2. A compound according to claim 1 wherein A represents a grouping of Formula III, $R^1$ represents the n-butyl group, $R^2$ represents a hydrogen atom or the methyl group, and the hydroxy radical attached to $C_{15}$ is in α-configuration.

3. A compound according to claim 1 which is 16-methylene-PGE₁ methyl ester and cyclodextrin clathrates thereof.

4. A compound according to claim 1 which is 16-methylene-13,14-dihydro-15(ξ)-PGE₁ and cyclodextrin clathrates and non-toxic salts thereof.

5. A compound according to claim 1 which is 16-methylene-PGF₁α methyl ester and cyclodextrin clathrates thereof.

* * * * *